US00PP09607P

United States Patent [19]

Christensen

[11] Patent Number: Plant 9,607

[45] Date of Patent: Jul. 23, 1996

[54] HYBRID ROSE PLANT NAMED 'CHRISNUSP'

[75] Inventor: Jack E. Christensen, Ontario, Calif.

[73] Assignee: Paramount Nursery Packaging Company, West Grove, Pa.

[21] Appl. No.: 311,541

[22] Filed: Sep. 15, 1994

[51] Int. Cl.[6] ..... H01H 5/00

[52] U.S. Cl. ..... Plt./11

[58] Field of Search ..... Plt./11, 12, 22

*Primary Examiner*—Howard J. Locker

[57] ABSTRACT

A hybrid rose plant having upright, vigorous growth intermediate between the grandiflora and miniature classes; fully double flowers of variable cream, pink and red hues; healthy dark green, lightly glossy foliage; and relatively few prickles on proportionately long stems.

1 Drawing Sheet

SUMMARY OF THE INVENTION

The present invention relates to a new and distinct hybrid rose cultivar intermediate between the Grandiflora and Miniature classes, which was originated by me by crossing an unnamed seedling of Love (U.S. Plant Pat. No. 4,437)× Picasso (U.S. Plant Pat. No. 3,351), with an unnamed seedling of Bluhwunder×MORpints.

The primary objective of this breeding was to produce a floriferous cultivar with red and white flowers that have both the striping of MORpints and the "banded" characteristics of Picasso.

This objective was substantially achieved, along with other desirable improvements, as evidenced by the following unique combination of characteristics which are outstanding in my new variety and which distinguish it from its parents as well as from all other varieties of which I am aware. For example, this new rose variety has:

1. Fully double red and cream flowers with variable blotching and banding and occasional striping;

2. A vigorous, upright growth habit which is intermediate between the Miniature and Grandiflora classes;

3. Long stems of good cutting quality;

4. Relatively few prickles.

The foregoing characteristics and distinctions come true to form via asexual reproduction and are established and transmitted through succeeding propagations by budding doen at Wasco, Calif., and by cuttings made at Ontario, Calif.

DESCRIPTION OF THE DRAWING

The accompanying illustration shows typical specimens of the flowers and vegetative growth of this new variety in different stages of development, depicted in color as nearly true as it is reasonably possible to make the same in a color portrayal of this nature.

DETAILED DESCRIPTION OF THE INVENTION

The following is a detailed description of my new rose variety, which has been given the denomination "CHRisnusp". Throughout this specification, color names beginning with a small letter convey ordinary dictionary significance for the color, while color names beginning with a capital letter designate values based on The Royal Horticultural Society Colour Chart, London, England.

The specimens used in making this description were grown outdoors at Ontario, Calif., in the month of May.

FLOWERS

The blooming habit is recurrent. The bud size is approximately three-fourths inch in length when the petals start to unfurl.

The bud form is ovoid.

The bud color when sepals first separate varies between cream and Orange Group 24D as the base color, overlaid with near Red Group 53A where exposed to sunlight.

When the bud is half open, the color on the upper side of the petals is cream, near Orange Group 19D, on the lower one third of the petal, and deep pink between Red Group 52A, and Red Group 54A on the outer two-thirds of the petal; while on the lower side of the petals it is between a creamy light pink near Red Group 38B and a deep pink near Red Group 51A.

The sepals vary from green to purple green in color. Their outer surface is smooth with scattered stipitate glands, while the inner surface is uniformly covered with a fine wooly tomentum; there are three lightly appendaged sepals and two unappendaged sepals with hairy edges.

The receptacle is near Yellow Green Group 144A in color and has a cylindrical-funnel shape, a smooth surface and is average in size.

The peduncle is relatively erect, of thin to average caliper, relatively long, and has a smooth surface with a few tiny prickles and stipitate glands; its color is light green to near Greyed Purple 187A.

The bud opens relatively slowly.

BLOOM

Bloom size is relatively small for the size of the bush, with an average open diameter of nearly two and one half inches. The blooms are borne singly and and in irregular clusters.

The stems are long and of normal strength.

When first open, the flower is high-centered in form, and the center remains pointed until the bloom is about half opened. The petals, which are moderately heavy in texture and broadly obovate in shape, average between 25 and 32 in number, and surround the pistils in layered and raised circular imbrications with a few irregular petaloids near the center.

When blooms are freshly opened, flower color, in general, is pink, near Red Group 55A, resulting from the combination of creamy veins and light red interveinal patches in the central area of the bloom, darkening more uniformly toward the perimeter to near Red Group 53B.

After three days the overall color effect is reddish, between Red Group 57A and Red Group 53B.

In newly opened flowers, the upper side of most petals is pink and cream, the inner third of the petals and many veins being cream, and the outer two-thirds being a mottled pink, between Red Group 55A and Red Group 53B, while the under side of most petals is cream to light pink, near Red Group 55D. Toward the base of the petals on both sides the color is light yellow, near Yellow Group 10D.

When the bloom is three days old, the color on the upper side of most petals is nearly white in the inner third, overlaid first in blotches then solidly toward the margin, where exposed to sunlight, with light red between Red Group 57A and Red Group 53B; the color on the reverse side of most petals is near white.

Colors are modified at times by being blotched, shaded, and/or striped with other colors.

The fragrance is light.

The blooms drop off cleanly, and last both on the plant and as cut flowers for a relatively long time.

REPRODUCTIVE PARTS

The anthers are abundant and small in size. The filaments are light golden yellow. The pollen is golden yellow. The stigmas are plate green in color, while their styles are light green, becoming a transulucent pink just under the stigmas.

PLANT

The plant becomes an upright bush, about three to three-and-a-half feet in height, and vigorous in growth.

FOLIAGE

The foliage is medium in size and abundant. New foliage is reddish green, and mature foliage is deep green with a lightly semi-glossy surface. A normal mid-stem leaf has five leaflets which are widely separated.

The leaflets are ovate in shape with a pointed apex; they are fairly leathery in texture, and their margins are finely and irregularly serrate.

The petiole rachis is green, sometimes with purple highlights, and has a few very small prickles on the underside and some stipitate glands along the edges of the grooved upper surface.

Stipules are serrated and of average length.

The foliage has better than average disease resistance, particularly with respect to mildew, under normal growing conditions at Ontario, Calif.

STEM

Newly developing stems are purplish or bronzy and sometimes have a few tiny prickles and/or stipitate glands. Stems that have borne flowers are green to purplish. Older, mature wood is green to gray with a rough bark.

There are very few large prickles and a few small prickles on the main basal canes and on the laterals to the blooming stems. These prickles are brown to gray in color, and are hooked slightly downward.

Young prickles on new growth are purplish in color.

PARENTAGE

The seed parent was an unnamed, undissemianted Grandiflora seedling which resulted from the cross of Lovex Picasso and which displayed the seasonal floral "banding" that is characteristic of its pollen parent.

The pollen parent was a different unnamed, undisseminated seedling, a miniature rose, which came from crossing Bluhwunder×MORpints and which featured the variable striping characteristics of its pollen parent in the flowers.

I claim:

1. A new and distinct variety of rose plant, substantially as shown and described herein, characterized particularly as to novelty by its unique combination of an upright, vigorous habit of growth, intermediate between the grandiflora and miniature classes; its fully double flowers of variable cream, pink and red hues; its healthy, dark green, lightly glossy foliage; and its relatively frw prickles on proportionately long stems.

* * * * *

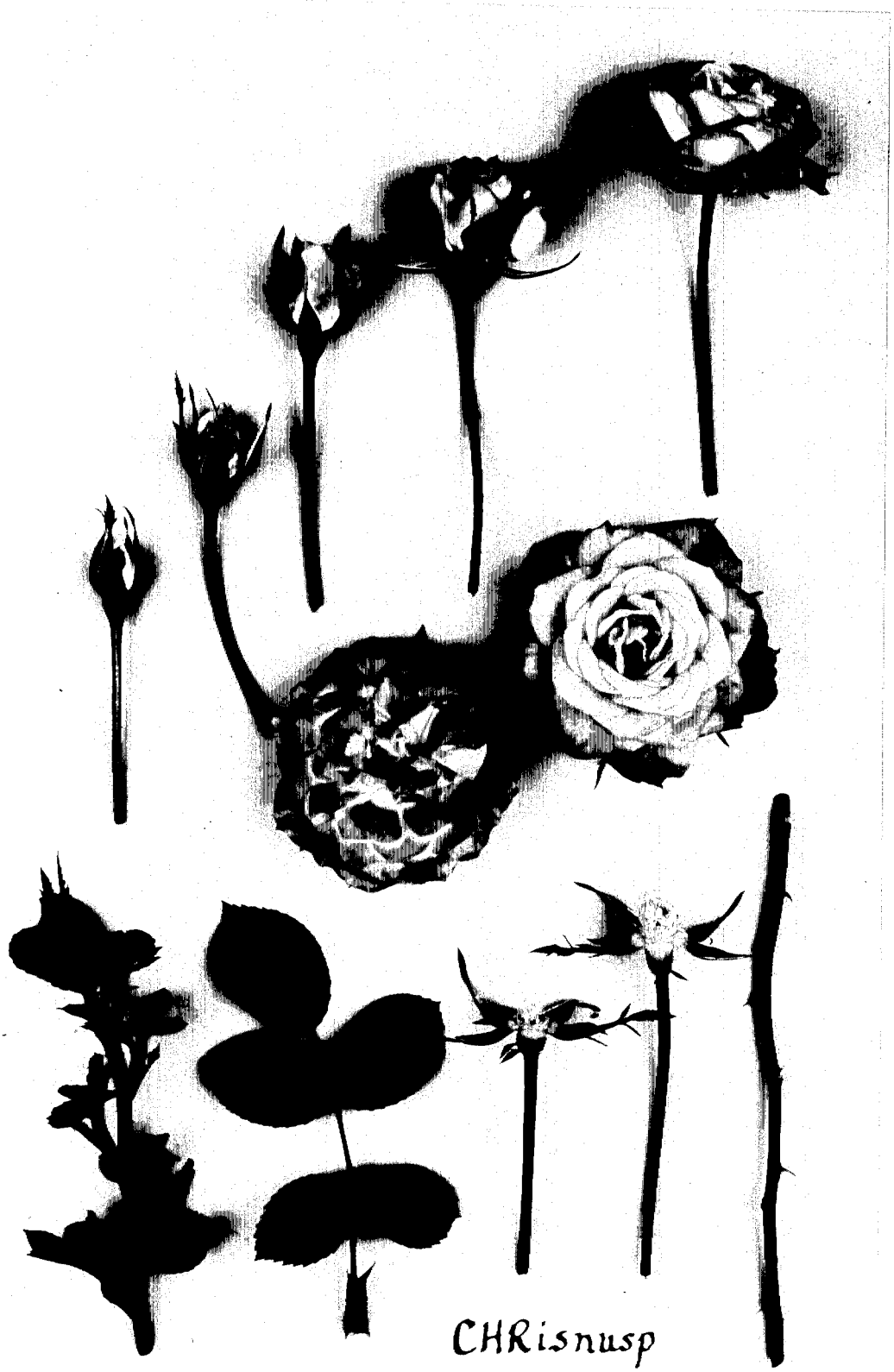
CHRisnusp